United States Patent [19]
Lewis et al.

[11] 4,068,524
[45] Jan. 17, 1978

[54] ULTRASONIC INSPECTION OF ARTICLES

[75] Inventors: Richard Lewis, Rushden; Michael J. Parker, Kettering, both of England

[73] Assignee: British Steel Corporation, London, England

[21] Appl. No.: 685,159

[22] Filed: May 11, 1976

[30] Foreign Application Priority Data

May 14, 1975 United Kingdom ............... 20402/75

[51] Int. Cl.² ........................................... G01N 29/04
[52] U.S. Cl. ........................................ 73/598; 73/611
[58] Field of Search ............... 73/67.7, 67.8 R, 67.8 S, 73/67.9

[56] References Cited

U.S. PATENT DOCUMENTS

| | | | |
|---|---|---|---|
| 3,033,029 | 5/1962 | Weighart | 73/67.8 R |
| 3,576,126 | 6/1969 | Weighart | 73/67.7 |

*Primary Examiner*—Jerry W. Myracle
*Attorney, Agent, or Firm*—Bacon & Thomas

[57] ABSTRACT

A method of ultrasonically inspecting an article comprises the following steps: transmitting a succession of ultrasonic pulses into the article; for each transmitted pulse, detecting and registering electrically the reflected pulse from the front surface of the article; detecting and registering electrically, with a predetermined gain, any reflected pulses indicative of faults or discontinuities within the article; detecting and registering electrically, again with a predetermined gain, at least the first reflected pulse from the rear surface of the article; monitoring the amplitudes of the registered reflected pulse from the front surface and at least the first reflected pulse from the rear surface of the article; and continuously controlling gains for succeeding pulses in dependence on the amplitude of the reflected pulse from the front surface of the article.

16 Claims, 8 Drawing Figures

ULTRASONIC INSPECTION OF ARTICLES

This invention relates to the ultrasonic inspection of articles with regular surfaces, for example, solid billets or tubes of metal.

According to the invention there is provided a method of ultrasonically inspecting an article comprising transmitting a succession of ultrasonic pulses into the article; for each transmitted pulse, detecting and registering electrically the reflected pulse from the front surface of the article; detecting and registering electrically, with a predetermined gain, any reflected pulses indicative of defects, faults or discontinuities within the article; detecting and registering electrically, again with a predetermined gain, at least the first reflected pulse from the rear surface of the article; monitoring the amplitudes of the registered reflected pulse from the front surface and at least the first reflected pulse from the rear surface of the article; and continuously controlling gains for succeeding pulses in dependence on the amplitude of the reflected pulse from the front surface of the article.

By means of the invention it is possible to detect faults or discontinuities within the article which produce reflected pulses and also defects which produce attenuation of transmitted pulses to such a degree as to reduce below predetermined threshold values at least the first reflected pulse from the rear surface of the article at approximately constant sensitivity.

The amplitude of the detected and registered reflected pulse from the front surface of the article may be maintained at a predetermined level by means of an automatic gain control system which may be applied to this reflected pulse and subsequent fault and rear surface reflected pulses.

The said gains may include at least one step gain superimposed on the automatic gain and applied to received reflected pulses after the reflected pulse from the front surface of the article.

In one embodiment of the invention the first and the second reflected pulses from the rear surface of the article are detected and registered electrically with predetermined gains. In this case a double step gain may be applied, i.e., a first step gain after the reflected pulse from the front surface and a second step gain after the first reflected pulse from the rear surface. In addition a time increasing ramp gain may be applied after one or both step gains.

The or each step gains may be arranged to be such as to raise the amplitude of the first reflected pulse from the rear surface of the article, or the first and second reflected pulses from the rear surface of the article, to the amplitude of the reflected pulse from the front surface of the article (with a defect free article).

The invention includes within its scope apparatus for carrying out the method defined herein.

In order that the invention may be more fully understood two embodiments thereof will now be described by way of example with reference to the accompanying drawings in which.

Figure 1:
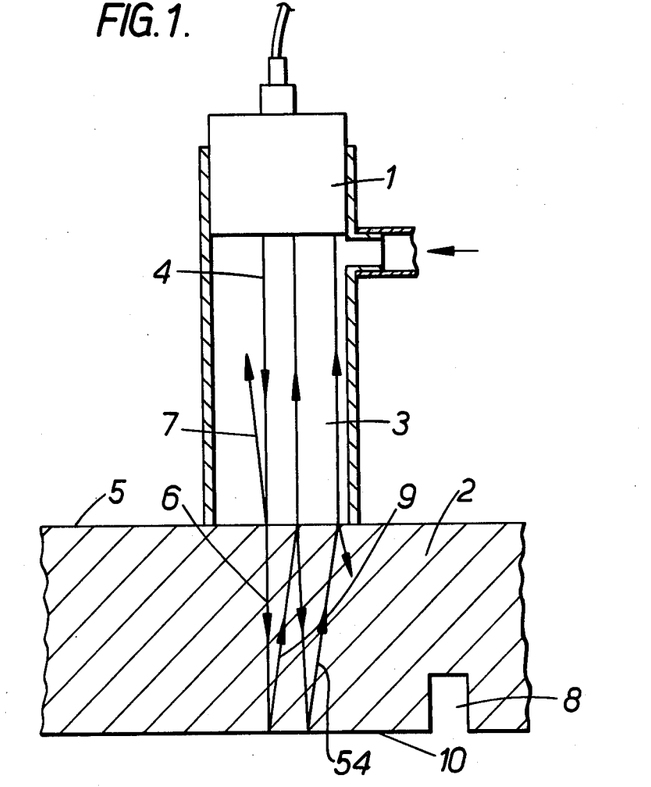
FIG. 1 is a diagrammatic side elevation of typical ultrasonic inspection apparatus.

As seen in FIG. 1 an ultrasonic transducer 1 is located at normal incidence to the surface of a testpiece 2 and the ultrasonic energy is coupled from the transducer to the testpiece by means of a water column 3.

In FIG. 1 the soundwave 4 emitted by the ultrasonic transducer 1 travels down the water column 3 and impinges on the surface 5 of the testpiece. At this latter interface a portion 6 of the soundwave energy is transmitted into the testpiece and the remainder 7 is reflected back up the water column towards the ultrasonic transducer. The soundwave which is transmitted into the testpiece can be used for the detection of discontinuities, for example, laminations, segregates, etc., which occur in the testpiece. In automatic systems the transducer configuration is traversed across the surface of the testpiece and the ultrasonic transducer is pulsed at high frequency which results in a series of inspection points across the surface of the testpiece.

Frequently the system is calibrated to a specific sensitivity by means of an artificial discontinuity 8 machined into a sample of material similar to that under test. This artificial discontinuity may be, for example, a 6 mm diameter, flat bottomed hole machined into the underside of the testpiece as shown in FIG. 1. The sensitivity of the electronics associated with the ultrasonic transducer is adjusted in sensitivity to detect the flat bottomed hole. The ultrasonic transducer assembly is then transferred to the testpiece and any signals received with amplitude in excess of that from the flat bottomed hole standard causes the testpiece to be rejected or laid aside. In addition to this requirement for calibration, under some circumstances it is required to monitor the amplitude of echo 9 reflected from the lower surface 10 of the testpiece and to use this echo amplitude as a measure of the attenuation of the soundwave propagating through the testpiece. If this amplitude falls in excess of a predetermined level, for example, 12dB, then the testpiece is again considered to be defective. Under this latter situation the loss of backwall echo from the testpiece can be related either to the presence of discontinuities in the material which have dispersed the ultrasonic soundwave, or, to the general condition of the product which has reduced the amount of energy coupled into the testpiece.

Figure 2:
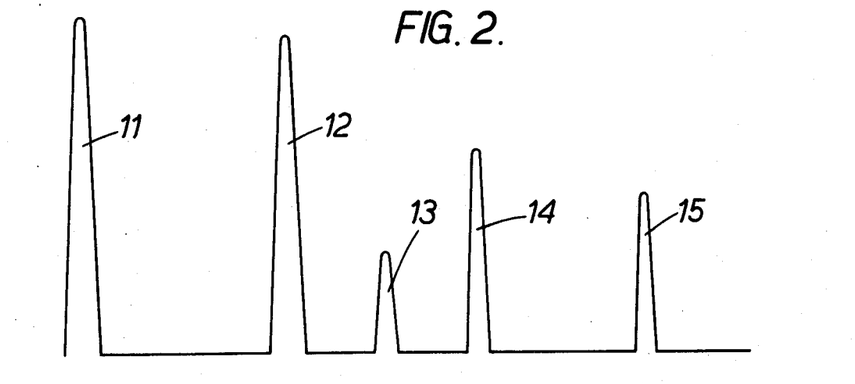
FIG. 2 shows an unmodified output signal waveform associated with the kind of apparatus shown in FIG. 1.

The ultrasonic signals obtained from the test configuration of FIG. 1 are shown in FIG. 2. In this latter figure reading from left to right, the signals are firstly the transmitter pulse 11 which corresponds to the moment at which the ultrasonic transducer is energized, a pulse 12 which arises from the interface between the water column and the testpiece outer surface, possibly a pulse 13 which arises from a discontinuity in the testpiece, a pulse 14 which is the first backwall echo from the testpiece and which arises from the bottom surface 10 of the testpiece and a pulse 15 which corresponds to the second backwall echo from the testpiece. This latter echo is the result of two traverses in each direction of the incident soundwave through the testpiece. Subsequent echoes are received by the ultrasonic transducer which correspond to further reverberations of the incident soundwave both in the testpiece and the water column. A suitable arrangement of the water column length in relation to the thickness of the testpiece ensures that these later echoes do not interfere with the basic echoes shown in FIG. 2.

Under typical testing conditions any additional echoes which occur in the time interval between the water testpiece interface echo and the first backwall echo from the testpiece, are due to discontinuities within the material. Furthermore, a reduction in amplitude of the first backwall echo is caused either by the presence of discontinuities within the testpiece or due to a change in the energy coupled into the testpiece.

With typical testing conditions the testpiece can be up to 100mm in thickness and the testpiece can be in the hot finished condition. Under these latter circumstances it is frequently found that the variation in amplitude of the first backwall echo is of the order of 24dB.

The main causes of the large variation in amplitude of the first backwall echo are primarily the roughness and general geometry associated with the upper and lower surfaces of the testpiece, the variation in angle of incidence of the ultrasonic beam impinging on the outer surface of the testpiece due to variations in the mechanics of the system which locates the ultrasonic transducer and finally the actual attenuation within the testpiece. The result of these preceding effects can be to obtain an ultrasonic inspection generally at a much lower sensitivity than indicated by the actual calibration standard.

Some techniques which have been applied to attempt to overcome this situation are as follows. The inspection system can be fitted with an automatic gain control (AGC) facility by means of which the first backwall echo 14 is maintained at a constant amplitude, i.e., as the actual amplitude of this echo varies, then the gain of the system is increased or decreased so that the observed amplitude of the echo signal is maintained constant. When this technique is applied it means that the reduction in first backwall echo cannot be measured directly and in order to monitor the attenuation due to the material, the amplitude of the second backwall echo 15 is compared to the first backwall echo.

The foregoing technique can be applied with reasonable success under certain circumstances, but the following disadvantages can be encountered in testing thicker specimens, particularly in the hot finished condition:

1. With thick testpieces, for example up to 100mm, the total attenuation of the ultrasonic wave in the material becomes large and the sensitivity of the system to small changes in geometry can result in considerable difficulty in obtaining a clear second backwall echo from the testpiece.

2. In the case of articles with hot finished surfaces or surfaces whose local irregularities exceed approximately one eighth of the wavelength of the testing ultrasonic waves, interference effects occur which can produce erroneous indications of attenuation if only two consecutive echoes amplitudes are monitored, e.g., the second backwall echo compared only to the first backwall echo.

3. The permitted thickness variation on some hot finished products can typically be of the order of $-12\frac{1}{2}\%$ to $+15\%$. The effect of this situation is that the position in time of the second backwall echo can vary by a considerable amount and its position must thus be monitored by means of an electronic gate of adequate width. The effect of using wide electronic time gates is two-fold, firstly the time during which defect echoes can be observed is automatically reduced and secondly, the possibility of multiple echoes occurring in the second backwall echo gate is also much increased. The latter situation then prevents a ratio being taken between the actual second backwall echo and the first backwall echo.

4. A circumstance can exist with the above technique whereby the first backwall echo is initially reduced in amplitude due to the presence of a small defect in the testpiece but the automatic gain control facility then increases the system sensitivity until the first backwall echo reaches the predetermined amplitude. This in turn means that the sensitivity of the system to defects in the testpiece has been increased, and it is now possible that the small defect which was sufficient to attenuate the first backwall echo, but not initially to give an echo of sufficient amplitude to trigger the equipment, after the increase in gain which is applied by the AGC facility then the echo amplitude obtained from the small defect could now be increased to level which is sufficient to trigger the defect gate, i.e., under these circumstances a very small defect has now been detected due to over-sensitivity of the system. The over-sensitivity being caused by the method of application of AGC.

The following describes the new techniques provided by the invention which very largely eliminate the disadvantages described in the preceding text. The basic difference between our new technique and the existing techniques is to use the water testpiece interface echo as part of the automatic gain control facility. The first embodiment of FIGS. 3 to 5 monitors the first backwall echo only from the article, and is particularly applicable with very thick samples where the second backwall echo is not always easily detected.

Figure 3:
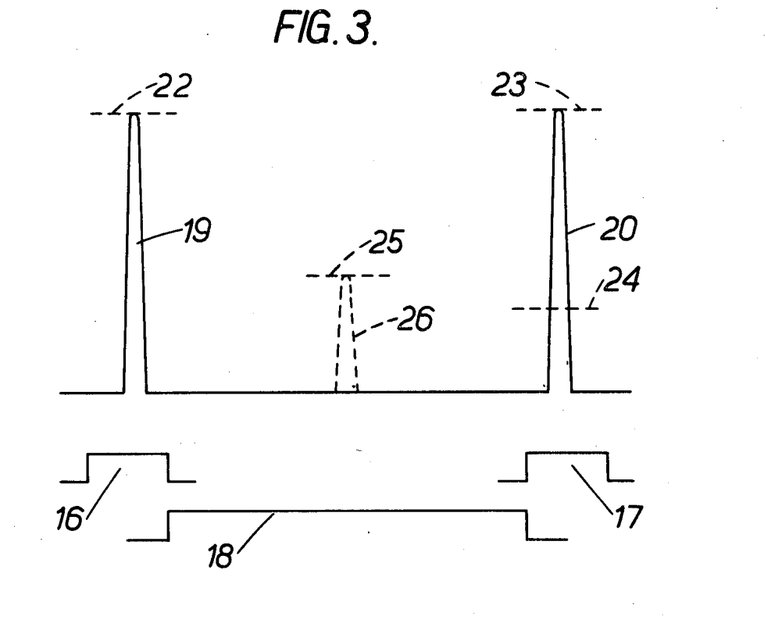
FIG. 3 shows an output signal waveform modified by means of a first embodiment of the present invention.

Experiments have shown that by suitable and reasonable selection of ultrasonic transducer diameter and frequency, and also water column length and diameter, it is possible to obtain a correlation between the amplitude of the water testpiece interface echo and the energy coupled into the testpiece. Having achieved this correlation then the mode of operation the first embodiment of the new system is as follows. There is shown in FIG. 3 the three electronic timegates which are generated by the system. Gate 16 monitors the amplitude of the water testpiece interface echo, Gate 17 monitors the amplitude of the first backwall echo and Gate 18 monitors the amplitude of echoes arising from within the body of the testpiece due to discontinuities. It is seen in FIG. 3 that the limits of Gate 18, the defect echo gate, are set by the end of Gate 16 and the start of Gate 17. Gates 16 and 17 are comparatively short in time and are just sufficient to encompass the corresponding echoes.

In practice, it is found that the absolute difference in amplitude between the water testpiece interface echo and the first backwall echo tends to be of the order of 20dB. This embodiment initially requires that these two latter signals are electronically equalized in amplitude. This situation is shown in FIG. 3 where the water testpiece interface echo 19 and the first backwall echo 20 as displayed on the equipment visual display unit are now of the same amplitude. This is achieved by means of a step gain characteristic which changes the gain by the required amount at the end of time Gate 16. This situation is shown at 21 in FIG. 4. For a given inspection situation, there exists a maximum obtainable amplitude of both water testpiece interface echo 19 and first backwall echo 20 and these are determined purely by the geometries of the situation. The magnitude of the step change 21 in the gain characteristic is adjusted until the maximum amplitudes of both water testpiece interface echo and first backwall echo are equal. Typically, these amplitudes are indicated by pre-set levels marked on the screen of the equipment visual display unit, as shown at 22 and 23 in FIG. 3. In practice, this situation is obtained with the ultrasonic transducer assembly traversing across the surface of a typical testpiece. It is quite easy to observe the maximum amplitudes of the two echoes concerned.

The automatic gain control of the system sensitivity is then achieved by maintaining either the water testpiece interface echo 19 or the first backwall echo 20 at the maximum amplitude determined by the initial setting-up by adjusting the overall gain of the system. Thus the basic difference between this embodiment of the invention and previous techniques is that with previous technique the first backwall echo would always be maintained at a maximum amplitude, whereas with our new system either the water testpiece interface echo 19 or the first backwall echo 20 is maintained at maximum amplitude. This technique is possible because of the correlation obtained between the water testpiece interface echo and the first backwall echo, and basically means the automatic gain control facility is being applied by the water testpiece interface echo and not the first backwall echo. This technique eliminates the problems encountered with the earlier method of application of AGC and also permits a more simple measurement of the attenuation obtained of the first backwall echo in the body of the testpiece. For example, a 12dB drop in the first backwall echo is measured relative to the water testpiece interface echo but with AGC applied as shown at 24 in FIG. 3. With previous systems this measurement was made by comparing the second backwall echo to the first backwall echo.

In order to calibrate the system for the detection of an artificial discontinuity, for example a flat bottomed hole, the ultrasonic transducer is traversed over the calibration standard and the trigger level 25 of Gate 18 is adjusted until the echo 26 from the calibration standard is sufficient to trigger the gate output see FIG. 3. This procedure is identical to conventional procedures. However, the presence of the automatic gain control facility means that it is not necessary to manufacture the calibration standard in a perfect piece of the testpiece. This latter situation has been confirmed as a result of measurements taken on a series of similar artificial defects made in a variety of positions on testpieces. These measurements showed a linear relationship between the amplitude of a water testpiece interface echo and the amplitude of the signal obtained from the artificial discontinuity.

Figure 4:
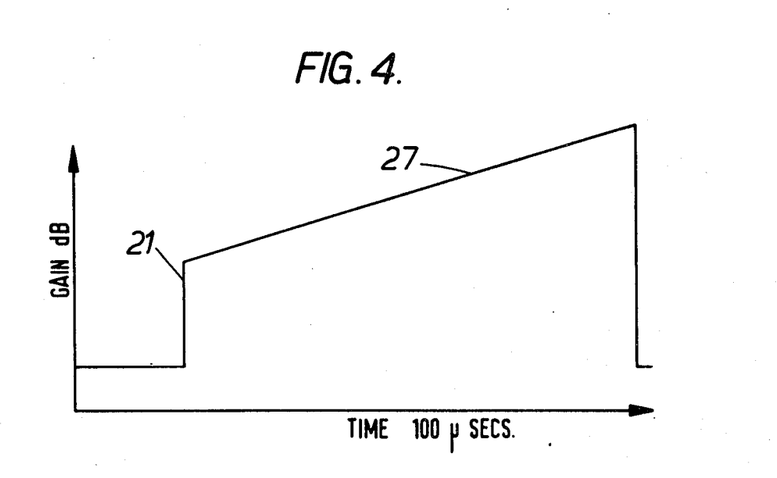
FIG. 4 shows a gain waveform of the kind applied by means of the first embodiment of the present invention.

An additional facility fitted to the new system is the use of a ramp gain characteristic immediately following the step change in gain, as shown at 27 in FIG. 4. The ramp gain characteristic enables the variation in amplitude of the first backwall echo due only to the changes in thickness of testpiece to be compensated for. A second additional facility is automatically to position the end of Gate 18 and the start of Gate 17. This latter adjustment is obtained by means of a measurement of the testpiece thickness immediately before the defect seeking ultrasonic transducer traverses across the testpiece, and obtains maximum width of the defect echo seeking Gate 18 during an inspection.

Typically, but not exclusively, a transducer for use with the invention would have a diameter of between 6mm and 20mm operating at a frequency of between 1MHZ and 5MHZ. The water column length would be up to 80mm, and water column diameter between 8mm and 24mm. In a particular example for use with inspecting tube of 6 inches diameter and larger, the transducer was of 15mm diameter operating at 2MHZ with a water column 37.5 mm long and 18mm in diameter.

Figure 5:
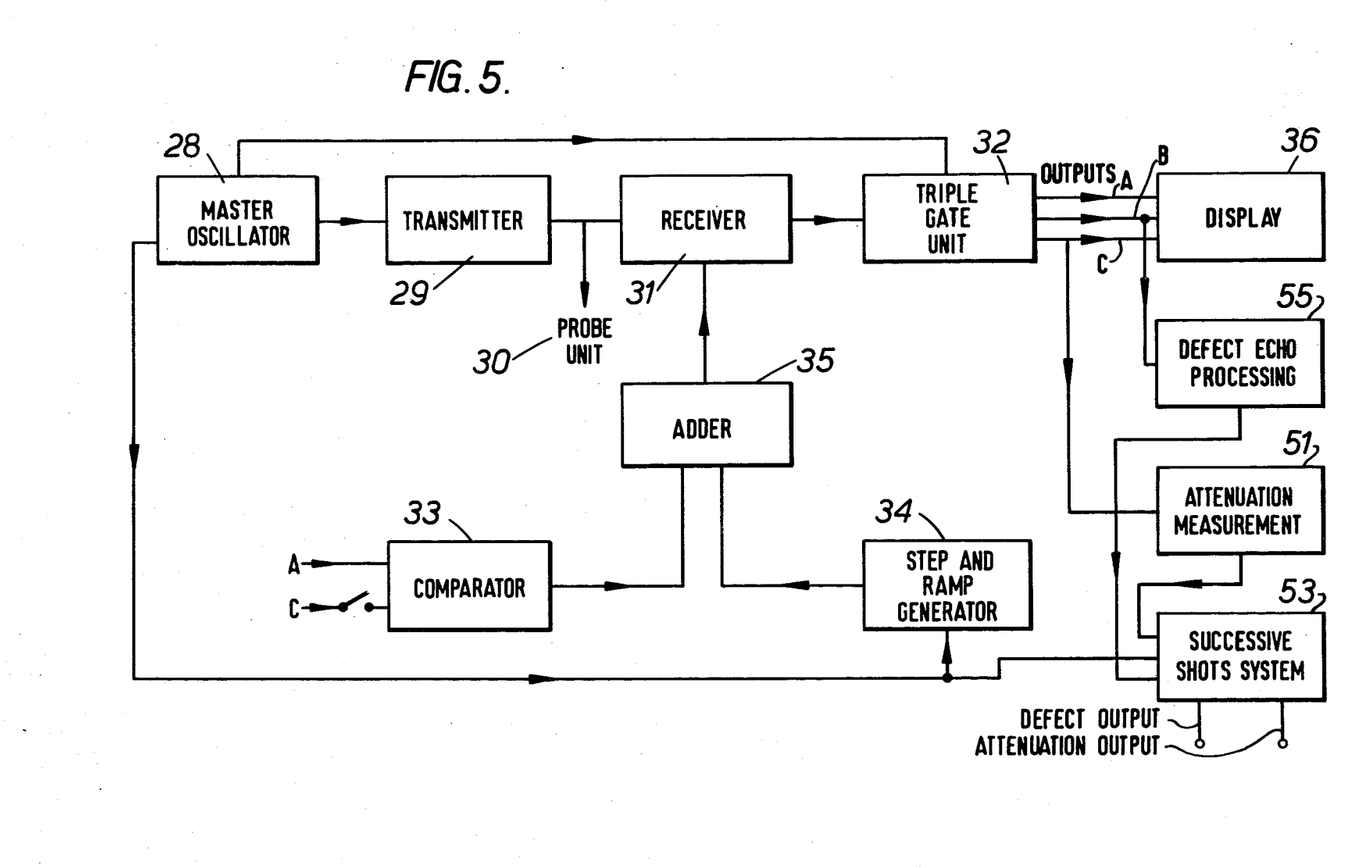
FIG. 5 is a block diagram of a circuit for operation of the apparatus of FIG. 1 in accordance with the first embodiment of the present invention.

Referring to the operational circuit shown in FIG. 5, a master oscillator 28 controls operation of a transmitter 29 which in turn actuates the testing probe unit 30. Echoes from the probe unit are processed by a receiver 31 and passed to a triple gate unit 32 controlled by Master oscillator 28 and having three outputs A, B and C related to the interface echoes, defect echoes, and first backwall echoes respectively. The outputs A and C are fed back to a comparator 33 where the overall AGC output voltage is set in dependence either on the larger of signals in A and C or on signal A only. At the same time generator 34 controlled by master oscillator 28, produces signals controlling the slope, step, time position and amplitude of the step and ramp gain. The signals from comparator 33 and generator 34 are combined in adder 35, the output of which is fed to receiver 31 for control purposes. As mentioned above signals from the receiver 31 are fed into the gate unit 32 which derives output voltages A, B, C proportional to the interface, defect and first backwall echo amplitudes. These output voltages are fed to a display unit 36. The defect output is fed to a defect echo processing unit 55, where the echo amplitude is discriminated. When a predetermined defect echo amplitude is exceeded, an output is fed to a successive shots system 53. This latter unit enables the duration of a defect echo to be measured and when a predetermined duration is exceeded, a final defect output is obtained.

The first backwall output from the gate unit 32 is fed into an attenuation measurement unit 51, controlled by master oscillator 28, where the attenuation of the first backwall echo relative to the interface echo is measured. Typically an output from unit 51 is obtained when the first backwall echo is attenuated by, e.g., 12dB or greater. Outputs from unit 51 to the successive shots system 53 are assessed for duration, as with defect echoes, and a final output provided.

The second embodiment of the invention illustrated (FIGS. 6 and 8) monitors both the first and second reflected pulses from the rear surface of the article (reference numerals 9 and 54 in FIG. 1) but is similar to the first embodiment, and the same reference numerals have been used in the FIGS. for corresponding integers.

Figure 6:
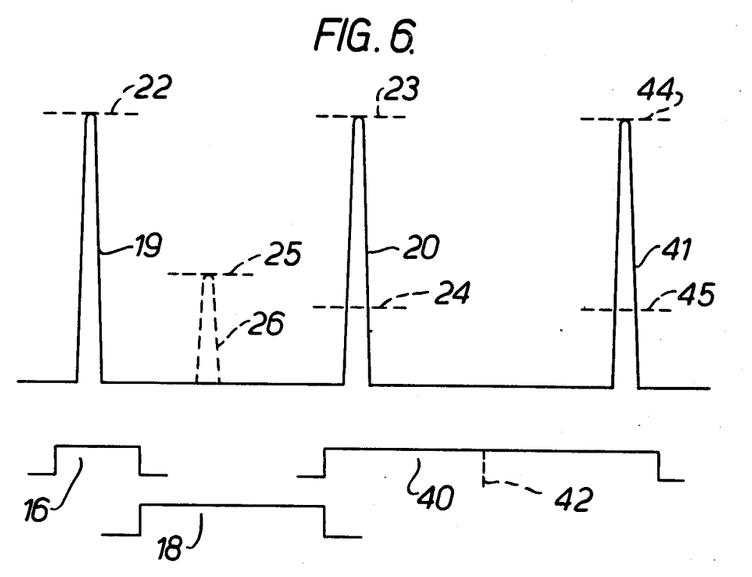
FIG. 6 shows an output signal waveform modified by means of a second embodiment of the present invention.

There is shown in FIG. 6 three electronic time gates which are generated by the system. Gate 16 monitors the amplitude of the water testpiece interface echo, Gate 40 is a double gate and monitors the amplitude of the first and second rear surface or backwall echoes and Gate 18 monitors the amplitude of echoes arising from within the body of the testpiece due to discontinuities. It is seen in FIG. 6 that the limits of Gate 18, the defect echo gate, are set by the end of Gate 16 and the start of Gate 40. Gate 6 is comparatively short in time and is just sufficient to encompass the interface echo.

Figure 7:
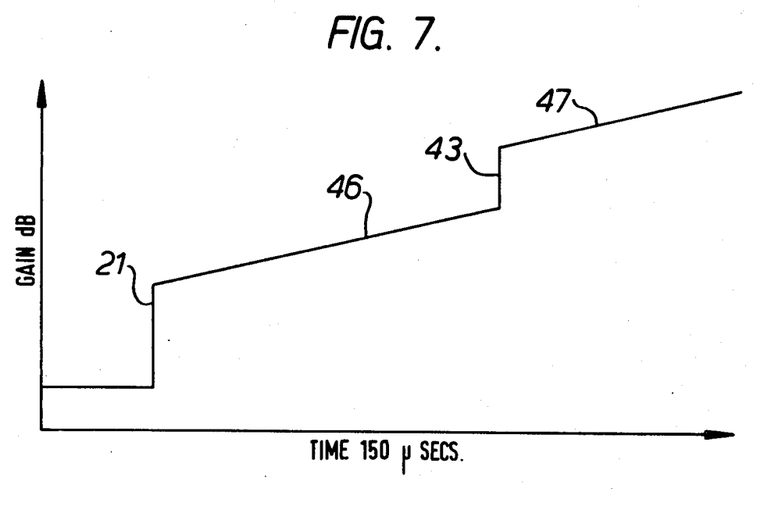
FIG. 7 shows a gain waveform of the kind applied by means of the second embodiment of the invention.

In practice, it is found that the absolute difference in amplitude between the water testpiece interface echo and the first backwall echo tends to be of the order of 20dB, and that between the first and second backwall echoes 5 to 10dBs. The system initially requires that these three echoes are electronically equalised in amplitude. This situation is shown in FIG. 6 where the water testpiece interface echo 19 and the first and second backwall echoes 20 and 41 as displayed on the equipment visual display unit are now of the same amplitude. This is achieved by means of a step gain characteristic which changes the gain by the required amounts at the end of time Gate 16 and at the midpoint 42 of Gate 40. This situation is indicated at 21 and 43 in FIG. 7. For a given inspection situation, there exists a maximum obtainable amplitude of water testpiece interface echo 19 and first and second backwall echoes 20 and 41 and these are determined purely by the geometries of the situation. The magnitude of the step changes 21 and 43 in the gain characteristics are adjusted until the maximum amplitudes of both water testpiece interface and first and second backwall echoes are equal. Typically, these amplitudes are indicated by pre-set levels marked on the screen of the equipment visual display unit, as shown at 22, 23 and 44 in FIG. 6.

The automatic gain control of the system sensitivity is then achieved by maintaining the water testpiece interface echo 19 at the maximum amplitude shown as 22 in FIG. 6.

This second embodiment has the same advantage over and difference with previous techniques as the first embodiment, and additionally has the advantage that for attenuation measurements the amplitudes of both first and second backwall echoes are monitored. For example, a 12dB drop in both first and second backwall echoes is measured relative to the water testpiece interface echo but with AGC applied, as shown at 24 and 45 in FIG. 6.

As with the first embodiment, the second embodiment incorporates ramp gain characteristics 46 and 47 (FIG. 7) immediately following step changes in gain 21 and 43, and also automatic positioning of the end of Gate 18 and the start of Gate 40 (FIG. 6).

Figure 8:
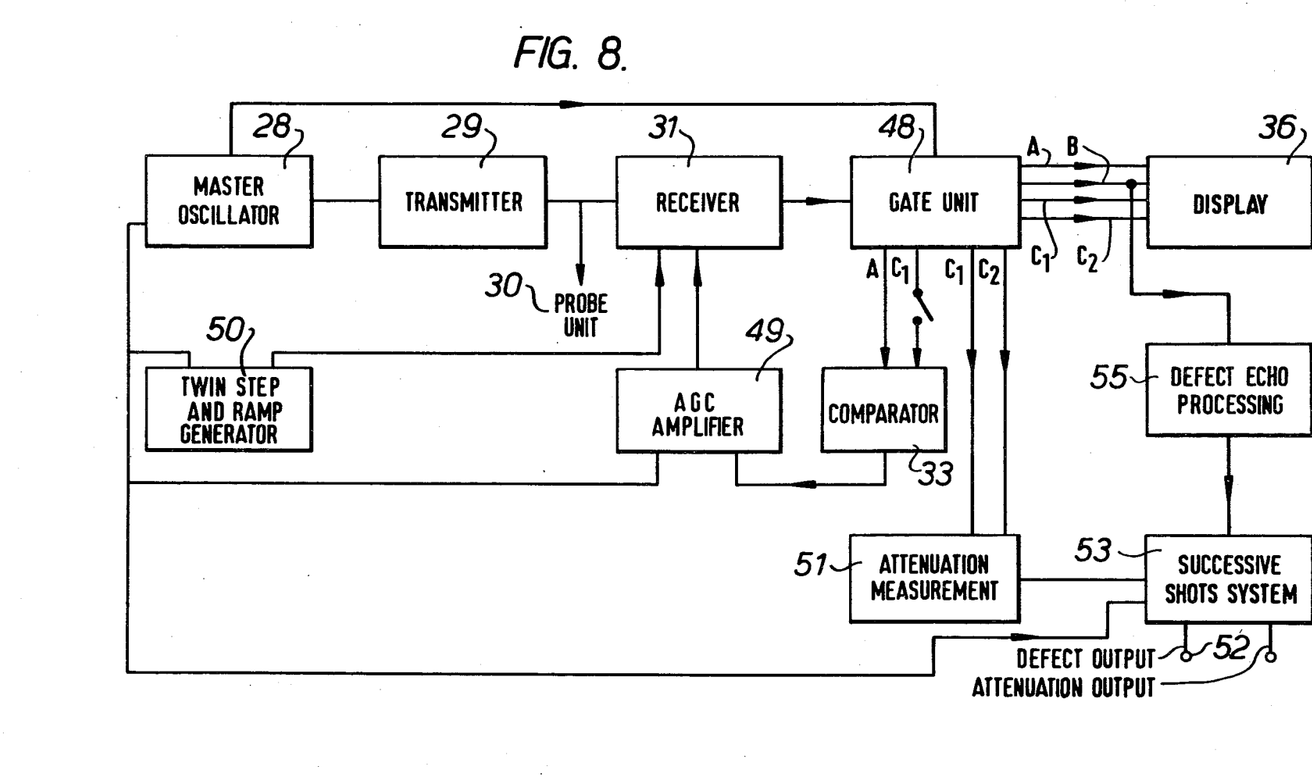
FIG. 8 is a block diagram of a circuit for operation of the apparatus of FIG. 1 in accordance with the second embodiment of the present invention.

Referring to the operational circuit shown in FIG. 8 a master oscillator 28 controls operation of a transmitter 29 which in turn actuates the testing probe unit 30. Echoes from the probe unit are processed by a receiver 31 and passed to a Gate unit 48 controlled by Master oscillator 28 and having four outputs A, B, C1 and C2 related to the interface echoes, defect echoes, and first and second backwall echoes respectively. The outputs A and C1 are fed to the comparator 33 and either the larger of signals A and C1 or signal A only is fed to a AGC amplifier 49 and sets the overall gain level. At the same time a generator 50 controlled by master oscillator 28, produces signals controlling the slope, time position and amplitudes of the steps in gain. Defect outputs from gate unit 48 are fed as in the first embodiment to display 36, defect echo processing 55 and successive shots system 53. The first and second backwall outputs C1 and C2 from gate unit 48 are passed to an attenuation measurement system 51 controlled by master oscillator 28. The attenuation measurement unit 51 simultaneously measures the attenuation of the first and second backwall echoes relative to the interface echo. Typically an output from unit 51 is obtained when the first and second backwall echoes are simultaneously attenuated by, e.g., 12dB or greater. The duration of an output from unit 51 is assessed by the successive shots system 53 as in the first embodiment.

We claim

1. A method of ultrasonically inspecting an article comprising transmitting a succession of ultrasonic pulses into the article; for each transmitted pulse, detecting and registering electrically the reflected pulse from the front surface of the article; detecting and registering electrically, with a predetermined gain, any reflected pulses indicative of faults or discontinuities within the article; detecting and registering electrically, again with a predetermined gain, at least the first reflected pulse from the rear surface of the article; monitoring the amplitudes of the registered reflected pulse from the front surface and at least the first reflected pulse from the rear surface of the article; and continuously controlling gains for succeeding pulses in dependence on the amplitude of the reflected pulse from the front surface of the article.

2. A method of ultrasonically inspecting an article comprising transmitting a succession of ultrasonic pulses into the article; for each transmitted pulse, detecting and registering electrically the reflected pulse from the front surface of the article; detecting and registering electrically, with a predetermined gain, any reflected pulses indicative of faults or discontinuities within the article; detecting and registering electrically, again with a predetermined gain, at least the first reflected pulse from the rear surface of the article; monitoring the amplitudes of the registered reflected pulse from the front surface and at least the first reflected pulse from the rear surface of the article; continuously controlling gains for succeeding pulses in dependence on the amplitude of the reflected pulse from the front surface of the article; and maintaining the amplitude of the detected and registered reflected pulse from the front surface of the article at a predetermined level by means of an automatic gain control system.

3. A method as claimed in claim 2 wherein the automatic gain control system is applied to the reflected pulse from the front surface of the article and to subsequent fault and rear surface reflected pulses.

4. A method as claimed in claim 2 wherein the said gains include at least one step gain superimposed on the automatic gain and applied to reflected pulses after the reflected pulse from the front surface of the article.

5. A method as claimed in claim 4 wherein the step gain is such as to raise, with a defect free article, the amplitude of the first reflected pulse from the rear surface to the amplitude of the reflected pulse from the front surface of the article.

6. A method as claimed in claim 5 wherein the amplitude controlling gains for succeeding pulses is taken either from the front surface of the article or from the first reflected pulse from the rear surface of the article.

7. A method as claimed in claim 2 wherein the first and second reflected pulses from the rear surface of the article are detected and registered electrically with predetermined gains.

8. A method as claimed in claim 7 wherein a first step gain is applied to reflected pulses after the reflected pulse from the front surface of the article and a second step gain is applied to reflected pulses after the first reflected pulse from the rear surface.

9. A method as claimed in claim 8 wherein the first and second step gains are such as to raise, with a defect free article, the amplitudes of the first and second reflected pulses from the rear surface of the article to the amplitude of the reflected pulse from the front surface of the article.

10. A method as claimed in claim 8 wherein a time increasing ramp gain is applied after each step gain.

11. A method as claimed in claim 2 wherein the gains are continuously adjustable.

12. Apparatus for ultrasonically inspecting an article comprising means for transmitting a succession of ultrasonic pulses into the article; means for each transmitted pulse, for detecting and registering electrically the reflected pulse from the front surface of the article; means for detecting and registering electrically, with a predetermined gain, any reflected pulses indicative of faults or discontinuities within the article; means for detecting and registering electrically, again with a predetermined gain, at least the first reflected pulse from the rear surface of the article; means for monitoring the amplitudes of the registered reflected pulse from the front surface and at least the first reflected pulse from the rear surface of the article; means for continuously controlling gains for succeeding pulses in dependence on the amplitude of the reflected pulse from the front surface of the article; and an automatic gain control system for maintaining the amplitude of the detected and registered reflected pulse from the front surface of the article at a predetermined level.

13. Apparatus as claimed in claim 12 wherein the automatic gain control system is applied to the reflected pulse from the front surface of the article and to subsequent fault and rear surface reflected pulses.

14. Apparatus as claimed in claim 12 including means for detecting and registering electrically the first and second reflected pulses from the rear surface of the article with predetermined gains.

15. Apparatus as claimed in claim 14 including means for applying a first step gain to reflected pulses after the reflected pulse from the front surface of the article and means for applying a second step gain to reflected pulses after the first reflected pulse from the rear surface.

16. Apparatus as claimed in claim 15 including means for applying a time increasing ramp gain after each step gain.

* * * * *